United States Patent
Marsman

(10) Patent No.: US 8,114,031 B2
(45) Date of Patent: Feb. 14, 2012

(54) FACILITATION OF ANTEGRADE INSERTION OF A GUIDEWIRE INTO THE SUPERFICIAL FEMORAL ARTERY

(76) Inventor: Johan Willem Pieter Marsman, Hilversum (NL)

( * ) Notice: Subject to any disclaimer, the term of this patent is extended or adjusted under 35 U.S.C. 154(b) by 248 days.

(21) Appl. No.: 12/374,919

(22) PCT Filed: Jul. 26, 2006

(86) PCT No.: PCT/NL2006/000388
§ 371 (c)(1), (2), (4) Date: Apr. 16, 2009

(87) PCT Pub. No.: WO2008/013441
PCT Pub. Date: Jan. 31, 2008

(65) Prior Publication Data
US 2009/0209943 A1 Aug. 20, 2009

(51) Int. Cl.
*A61M 25/00* (2006.01)
(52) U.S. Cl. .................................................... 600/585
(58) Field of Classification Search ................ 600/585; 604/164.01, 164.08, 164.09, 164.11, 164.13, 604/165.01, 165.04
See application file for complete search history.

(56) References Cited

U.S. PATENT DOCUMENTS

| | | | |
|---|---|---|---|
| 4,610,674 A | 9/1986 | Suzuki et al. |
| 4,726,369 A | 2/1988 | Mar |
| 4,829,999 A | 5/1989 | Auth |
| 4,850,960 A | 7/1989 | Grayzel |
| 4,858,810 A | 8/1989 | Intelkofer et al. |
| 4,876,126 A | 10/1989 | Takemura et al. |
| 4,925,445 A | 5/1990 | Sakamoto et al. |
| 4,957,117 A | 9/1990 | Wysham |
| 5,037,391 A | 8/1991 | Hammerslag et al. |
| 5,219,332 A | 6/1993 | Nelson et al. |
| 5,221,257 A | 6/1993 | Rosenbloom et al. |
| 5,312,338 A | 5/1994 | Nelson et al. |
| 5,423,331 A | 6/1995 | Wysham |
| 5,728,148 A | 3/1998 | Bostrom et al. |

(Continued)

FOREIGN PATENT DOCUMENTS

DE 201 07 131 U1 8/2001

(Continued)

OTHER PUBLICATIONS

Saddekni S, Srur M, Cohn DJ, Rozenblit G, Wetter EB, Sos TA. Antegrade catheterization of the superficial femoral artery. Radiology. Nov. 1985;157(2):531-2.

(Continued)

*Primary Examiner* — Jeffrey G Hoekstra
(74) *Attorney, Agent, or Firm* — Leydig, Voit & Mayer Ltd.

(57) ABSTRACT

A guidewire for antegrade guidance of vascular interventions of a lower limb artery via a common femoral artery into a superficial femoral artery of a human patient. When in unloaded condition, the guidewire has, at its distal end, a rounded or floppy tip (4). A curved deflection section (5) is located closely proximal of the tip (4) and extends over an angle of curvature such that the rounded tip (4) is spaced from a continuation of an axis of a section proximally neighboring the curved deflection section (5). The curved deflection section (5) has a flexibility causing the curved deflection section (5) to spring back to substantially its original shape after elastic deformation to a straightened condition. A rotation preventer, a kit and a method for facilitating insertion of a guidewire into the superficial femoral artery are also described.

8 Claims, 4 Drawing Sheets

U.S. PATENT DOCUMENTS

| | | | |
|---|---|---|---|
| 5,851,189 | A | 12/1998 | Forber |
| 6,500,130 | B2 | 12/2002 | Kinsella et al. |
| 6,936,015 | B2 | 8/2005 | Esashi et al. |
| 2001/0016712 | A1 | 8/2001 | Hamilton |
| 2004/0073141 | A1 | 4/2004 | Hartley et al. |
| 2005/0261667 | A1 | 11/2005 | Crank et al. |

FOREIGN PATENT DOCUMENTS

| | | | |
|---|---|---|---|
| DE | 102 55 030 A1 | 6/2004 | |
| EP | 0 510 624 A1 | 4/1992 | |
| EP | 0 778 039 A1 | 6/1997 | |
| EP | 1 607 035 A1 | 12/2005 | |
| JP | 11-089940 | 4/1999 | |
| JP | 11-137693 | 5/1999 | |
| WO | WO 99/16495 A1 | 4/1999 | |
| WO | WO 00/10636 A1 | 3/2000 | |
| WO | WO 01/17601 A1 | 3/2001 | |
| WO | WO 02/094365 A1 | 11/2002 | |
| WO | WO 2004/018031 A2 | 3/2004 | |
| WO | WO 2005/072807 A1 | 8/2005 | |
| WO | WO 2006/065909 A1 | 6/2006 | |
| WO | WO 2008/013441 A1 | 1/2008 | |

OTHER PUBLICATIONS

Yeow KM, Toh CH, Wu CH, Lee RY, Hsieh HC, Liau CT, Li HJ. Sonographically guided antegrade common femoral artery access. J Ultrasound Med. Dec. 2002; 21 (12):1413-6.

Berman HL, Katz SG, Tihansky DP. Guided direct antegrade puncture of the superficial femoral artery. AJR Am J Roentgenol. Sep. 1986; 147(3):632-4.

Teitelbaum GP, Joseph GJ, Matsumoto AH, Barth KH. Double-guide-wire access through a single 6-F vascular sheath. Radiology. Dec. 1989; 173(3):871-3.

Thomas HG, Woodham CH. Technical report: use of a directional needle for antegrade guide wire placement when performing femoropopliteal angioplasty. Clin Radiol. Oct. 1993;48(4):278-9.

Dudeck O, Teichgraeber U, Podrabsky P, Lopez Haenninen E, Soerensen R, Ricke J. A randomized trial assessing the value of ultrasound-guided puncture of the femoral artery for interventional investigations. Int J Cardiovasc Imaging. Oct. 2004;20(5):363-8.

Hartnell G. An improvised reversal technique from retrograde to antegrade femoral artery cannulation. Cardiovasc Intervent Radiol. Nov.-Dec. 1998; 21(6):512-3.

Patel YD. Catheter for conversion of retrograde to antegrade femoral artery catheterization. AJR Am J Roentgenol. Jan. 1990;154(1):179-80.

Adam DJ, Beard JD, Cleveland T, Bell J, Bradbury AW, Forbes JF, Fowkes FG, Gillepsie I, Ruckley CV, Raab G, Storkey H; BASIL trial participants. Bypass versus angioplasty in severe ischaemia of the leg (BASIL): multicentre, randomised controlled trial. Lancet. Dec. 3, 2005;366(9501):1925-34.

Kannel WB. The demographics of claudification and the aging of the American population. Vasc Med. 1996;1(1): 60-4.

Kugler CF, Rudolfsky G. The challenges of treating peripheral arterial disease. Vasc Med. May 2003;8(2):109-14.

Kikkawa K. A new antegrade femoral artery catheter needle set. Radiology. Jun. 1984;151(3):798.

Saltzman J, Probst P. A new puncture needle (Seldinger technique) for easy antegrade catheterization of the superficial femoral artery. Eur J Radiol. Feb. 1987;7(1):54-5.

Bohndorf K. Gunther RW. A new catheter configuration for selective antegrade catheterization of the superficial femoral artery: technical note. Cardiovasc Intervent Radiol. Mar.-Apr. 1991;14(2):129-31.

Hawkins JS, Coryell LW, Miles SG, Giovannetti MJ, Siragusa RJ, Hawkins IF Jr. Directional needle for antegrade guide wire placement with vertical arterial puncture. Radiology. Jul. 1988;168(1):271-2.

Oestmann JW, Majewski A, Wilken B. Use of a modified needle in antegrade transfemoral arterial approach for diagnostic and interventional procedures. Eur J Radiol. Nov. 1988;8(4):261-25.

Bishop AF, Berkman WA, Palagallo GL. Antegrade selective catheterization of the superficial femoral artery using a movable-core guide wire. Radiology. Nov. 1985;157(2):548.

Sacks D, Summers TA. Antegrade selective catheterization of femoral vessels with a 4-or 5-F catheter and safety wire. J Vasc Interv Radiol. Aug. 1991;2(3):325-6.

Spijkerboer A.M., Scholten F.G., Mali W.P.T.M., van Schaik J.P.J. Antegrade Puncture of the Femoral Artery: Morphology Study. Radiology. 1990; 176:57-60.

Gay D.A.T., Edwards A.J., Puckett M.A., Roobottom C.A. A comparison of a "J" wire and a straight wire in successful antegrade cannulation of the superficial femoral artery. Department of Radiology, Derriford Hospital, Plymouth UK. Clinical Radiology (2005) 60, 112-115.

International Search Report and Written Opinion for PCT/NL2006/000388 dated May 8, 2007.

SACKS, *The Transatlantic Inter-Society Consensus (TASC). Management Of Peripheral Arterial Disease'*: J Vasc Interv Radio 14:S351 (2003).

FACILITATION OF ANTEGRADE INSERTION OF A GUIDEWIRE INTO THE SUPERFICIAL FEMORAL ARTERY

FIELD AND BACKGROUND OF THE INVENTION

The invention relates to a guidewire and a rotation preventer for facilitating antegrade catheterization of the superficial femoral artery (SFA) and to a method for inserting a guidewire into the SFA.

For introducing a catheter into the SFA, first the common femoral artery (CFA) is pierced with a vascular access needle. Next, a guidewire is inserted via the needle into the CFA and then manipulated so as to enter the SFA. This is followed by withdrawing the vascular access needle, leaving the inserted guidewire in place. Next, an introducer passing over and covering sections of the guidewire is inserted into the CFA and, guided by the guidewire, into the SFA. The guidewire is then withdrawn, leaving the introducer in the blood vessel, via which a catheter or other device for vascular intervention in a lower limb can be introduced into the SFA to the section of the SFA to be treated.

A particular problem associated to the introduction of a guidewire into the SFA is that the position where the arteries are close to the skin, allowing the needle to be reliably pierced through the skin and into the artery, is located nearby and on a side opposite of the position where the deep femoral artery (DFA) branches off from the CFA. More in particular, the position of the point of entry of the needle is dictated by requirements concerning access, staying clear of the abdominal cavity and the presence of bony tissue closely behind the artery allowing to clamp off the CFA in the event of bleeding and it cannot be seen from the outside of the patient what the distance is between the point of entry and the bifurcation of the CFA into the DFA and the SFA (see *Antegrade Puncture of the Femoral Artery: Morphologic Study* (Spijkerboer A. M., Scholten F. G., Mali W. P., Van Schaik J. P.; Radiology 1990 July; 176(1):57-60)). Accordingly, particular care and skill are required to manipulate the guidewire such that it enters the SFA.

The need of prolonged manipulation to gain access to the SFA is particularly disadvantageous, because fluoroscopic monitoring of the movements of the guidewire near the puncture area involves irradiating an area close to the area where the hands of the operator operating the needle and the guidewire are located, which entails repeated exposure of body parts of operators who regularly perform antegrade catheterization of the SFA. Many solutions have been proposed to facilitate leading a guidewire into the SFA.

In "*A New Antegrade Femoral Artery Catheter Set*" (Kikkawa K.; Radiology 1984 June; 151(3):798) a catheter needle set is described, which includes a polyethylene catheter sheath with a 30° angled tip and a steering device at the base for torque control. Introduction of this sheath into the SFA requires several test injections of contrast medium and a very subtle manipulation of the sheath under fluoroscopy guidance.

In "*A New Catheter Configuration for Selective Antegrade Catheterization of the Superficial Femoral Artery: Technical Note*" (Bohndorf K. Gunther R. W.; Cardiovasc Intervent Radiol. 1991 March-April; 14(2):129-31) a special polyethylene catheter with a very short (4 mm), 90° angled tip and one small side hole is proposed. After puncture of the CFA, a J-guidewire is introduced and the special catheter is advanced over the guidewire until the angled tip is in the CFA. Under fluoroscopic control and using small amounts of contrast medium this catheter is gently manipulated in the CFA until the tip is aligned with the CFA and directed towards the SFA. Then the SFA entrance is visualized and a guidewire with long floppy end is introduced via the catheter and directed into the SFA by the angled tip.

A needle having a curved distal end (J-needle) for directing a guidewire into the SFA is described in "*A New Puncture Needle (Vascular access Technique) for Easy Antegrade Catheterization of the Superficial Femoral Artery*" (Saltzman J., Probst P.; Eur J. Radiol. 1987 February; 7(1):54-5).

Also in "*Directional Needle for Antegrade Guidewire Placement with Vertical Arterial Puncture*" (Hawkins J. S., Coryell L. W., Miles S. G., Giovannetti M. J., Siragusa R. J., Hawkins I. F. Jr.; Radiology. 1988 July; 168(1):271-2) a needle for directing the guidewire to the SFA is proposed. The needle has a closed pencil-point tip and a distal side hole. This technique requires very subtle needle retraction, needle rotation and needle removal, fluoroscopic control, and the use of contrast medium in order to allow a guidewire to advance into the SFA.

In "*Double-Guide-Wire Access through a Single 6-F Vascular Sheath*" (Teitelbaum G. P., Joseph G. J., Matsumoto A. H., Barth K. H.; Radiology. 1989 December; 173(3):871-3), it is described to introduce a 6-F vascular sheath into the DFA over a 3 mm J-guidewire. This sheath is slowly withdrawn while injecting small amounts of contrast medium until its distal tip lies just proximal to the femoral bifurcation. Subsequently a second steerable guidewire (Glidewire) is manipulated through the sheath into the SFA; then the J-guidewire is removed and the sheath advanced into the SFA.

One technique described in "A Comparison of a 'J' Wire and a Straight Wire in Successful Antegrade Cannulation of the Superficial Femoral Artery" (Gay D. A., Edwards A. J., Puckett M. A., Roobottom C. A.; Clin Radiol. 2005 January; 60(1):112-5), is to introduce a 3 mm J-guidewire after standard antegrade puncture of the CFA with its tip facing anteriorly promoting passage into the SFA. However, in 6 of 25 patients in the experiment the guidewire did not enter the SFA correctly in the initial pass.

In spite of all efforts, a reliable technique for SFA cannulation after antegrade CFA puncture and without monitored manipulation is still lacking. In view of the problems associated with antegrade CFA puncture, some centers recently advocated the use of ultrasound-guidance to assist in antegrade CFA puncture and SFA cannulation. Also, the difficulties with antegrade catheterization of the SFA have led to the development of techniques for gaining access to the SFA via retrograde CFA puncture. All these reversal techniques in fact convert an ipsilateral retrograde puncture to antegrade catheterization. These techniques require a substantially longer screening time resulting in a higher radiation exposure than antegrade puncture techniques. In addition reversal may induce a greater stretch on the punctured vessel wall leading to hemorrhagic complications.

SUMMARY OF THE INVENTION

It is an object of the present invention to provide a solution which allows reliable entry of the SFA for antegrade cannulation of the SFA following an antegrade puncture, without requiring manipulations monitored using fluoroscopic screening and contrast medium injections.

According to one aspect of the invention, this object is achieved by providing a guidewire and a method for using the guidewire. The curved deflection section allows the rounded tip of the guidewire to be urged away from the DFA and into the SFA, so that the guidewire reliably enters the SFA without requiring monitored manipulation. More in particular, because the area where the tip of the guidewire is to be deflected in the direction in which the SFA diverges from the DFA is close to the area where the operators grips the guidewire, on the one hand, the direction of curvature of the curved deflection section can be controlled easily without relying on X-ray vision to actually see where the guidewire tip is and, on the other hand by avoiding the need of manipulation, contrast medium injection and fluoroscopic screening near the puncture site, exposure of the operator's fingers to X-ray radiation is substantially reduced.

The invention can also be embodied in a rotation preventer. Such a rotation preventer is particularly helpful for easily and reliably holding the guidewire in an orientation with the direction of curvature of the curved deflection section towards the SFA by reference to a surface outside the patient, such as for instance an outer abdominal skin surface of the patient.

The invention may also be embodied in a kit in which the distance of at least insertion depth markings to the tip of the guidewire corresponds to the length of the needle and, optionally, plus the length of the straightener in such a manner, that alignment of that marking with a predetermined part of the optional straightener, the needle or a hub of the needle indicates the location of the tip of the guidewire relative to the distal tip of the needle.

The invention may further be embodied in a guidewire in which the at least one humanly visible steering aid marking indicating the direction of curvature of a curved section of a distal end portion of the guidewire, so that the direction of curvature to which the curved section of the distal end portion springs back as it emerges from the distal tip of the needle can easily be pointed anteriorly towards the SFA.

Particular elaborations and embodiments of the invention are set forth in the dependent claims.

Further features, effects and details of the invention appear from the detailed description and the drawings.

DETAILED DESCRIPTION OF EMBODIMENTS

In FIGS. 1-7, examples of a guidewire 1 and of a rotation preventer 2 according to the invention are shown. The guidewire is specifically designed for antegrade insertion via a CFA into a SFA of a human patient and for subsequently guiding a catheter or a catheter introducer sheath into the SFA.

Figure 5:
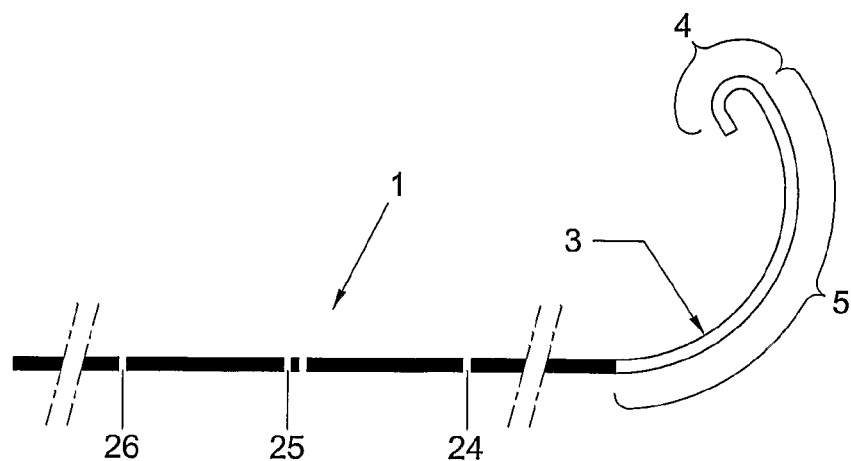
FIG. 5 is an enlarged side view of the distal end portion of the guidewire shown in FIGS. 1-3 in unloaded condition.

The guidewire 1 has a distal end portion 3 (in FIGS. 3 and 5, the white section) which is more flexible than a more proximal portion 7 of the guidewire 1. As is best seen in FIGS. 3 and 5, when in unloaded condition, for instance lying on a flat surface, the distal end portion 3 of the guidewire 1 is composed of a rounded tip 4 at its distal end and a curved deflection section 5 located proximally of the rounded tip 4.

The rounded tip 4 has a radius $R_4$ larger than the outer radius of the guidewire cross-section. The purpose of the rounded tip 4 is to reduce the risk of damaging the wall of an artery in which the guidewire 1 is advanced. In the guidewire 1 according to the present example, the rounded tip is formed by a curved tip section having a radius $R_4$ of 2 mm radius, the curvature extending over 180°. The curved tip section 4 preferably extends over at least 90° and more preferably at least 130° to reduce the risk of the extreme distal end of the guidewire damaging a wall of an artery particularly effectively and the curvature of the tip section preferably has a radius of 1-4 mm so that on the one hand the radius is wide enough to effectively prevent damage of the arteries and allow elastic deformation into a fully straightened condition while, on the other hand the radius is small enough to easily slip into the SFA. The curved tip section 4 has a flexibility which allows elastic deformation to a straightened condition, so that it will spring back to substantially its original shape when released after having been straightened during passage through a vascular access needle.

Preferences regarding the outer diameter of the guidewire are: at least 0.025 (0.64 mm), at most 0.05 inch (1.27 mm) and, more preferably, at least 0.035 inch (0.89 mm) and at most 0.038 inch (0.97 mm). Such diameters are most suitable for antegrade cannulation of the SFA.

Figure 1:
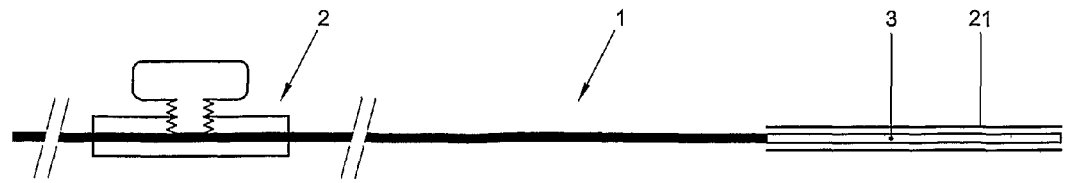
FIG. 1 is a schematic side view of a guidewire and a rotation preventer according to the invention, a distal end portion of the guidewire being located in a straightener.
Figure 2:
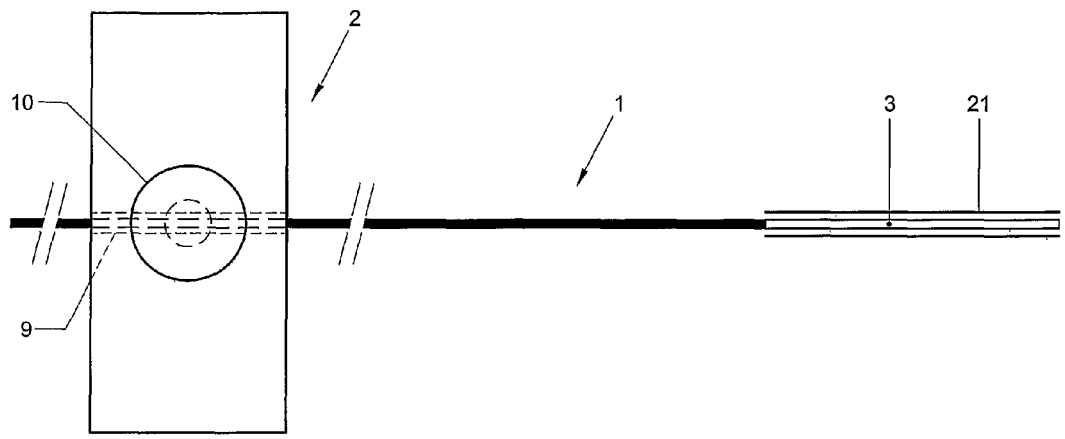
FIG. 2 is a top plan view of the arrangement shown in FIG. 1.
Figure 3:
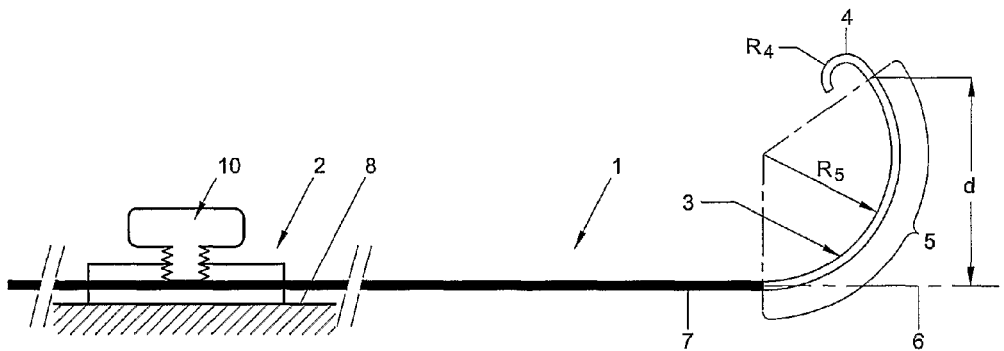
FIG. 3 is a side view as shown in FIG. 1, but with a distal section of the guidewire projecting in unloaded condition.
Figure 4:
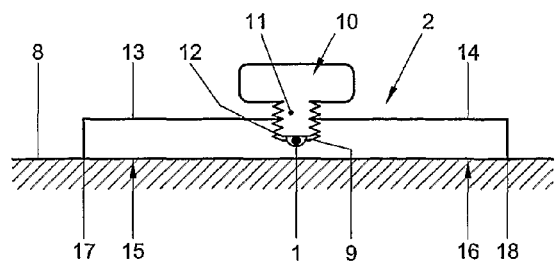
FIG. 4 is a frontal view of the rotation preventer shown in FIGS. 1-3.

As is best seen in FIG. 3, the curved deflection section 5 extends over an angle of curvature such that the rounded tip 4 is spaced over a distance d from a continuation 6 of an axis of a section 7 proximally neighboring the curved deflection section 5. The curved deflection section 5 has a flexibility causing the curved deflection section 5 to spring back to substantially its original shape when released after elastic deformation to a straightened condition as shown in FIGS. 1 and 2. The rounded tip 4 and the curved deflection section 5 are preferably curved in the same direction of curvature diverging from the continuation 6 of the axis of a section 7 proximally neighboring the curved deflection section 5.

The rotation preventer 2 is holding the guidewire 1 in a substantially constant orientation about its axis relative to a guide 8. A slight amount of rotational freedom may be allowed, for instance due to torsional flexibility of the guidewire 1 and/or tilting of the preventer relative to the guide 8. The preventer 2 bounds a passage 9 for accommodating a section of the guidewire 1 and is equipped with a guidewire retainer 10 for retaining the guidewire in the passage 9 against rotation about its axis relative to the rotation preventer 2. In the present example, the retainer is formed by a bolt 10 having a threaded shaft 11, which engages a threaded hole 12. When the bolt is screwed into the hole and tightened while a guidewire extends through the passage, the guidewire 1 is fixedly and releasably clamped in the passage 9.

In the present example, support arms 13, 14 extend on diametrically opposite sides of the passage 9 and forming support areas 15, 16 of which most distal ends 17, 18 are spaced apart in a direction transverse to the passage 9 and positioned for simultaneously contacting the substantially flat support surface 8 underneath the guide 2. In the present example, this surface 8 forms the guide. For reliably preventing the rotation preventer 2 from leaning over when it rests on a more or less flat and horizontal surface such as the surface 8, the span between the ends 17, 18 of the support areas 15, 16 remote from each other is preferably at least 3 cm and more preferably at least 5 cm. To avoid that the rotation preventer hinders advancement of the guidewire 1, its span is preferably smaller than 15 cm. In the present example, the span between the ends 17, 18 of the support areas 15, 16 is about 10 cm. When placing the rotation preventer 2 on a more or less horizontal surface 8, any torque exerted by the guidewire 1 onto the rotation preventer 2 will be insufficient to cause the rotation preventer 2 to tilt by lifting one side from the surface 8.

An example of a procedure of antegrade insertion of a guidewire 1 via a CFA into an SFA of a human patient 19 is described with reference to FIGS. 7A-7E.

First, the guidewire 1 is fixed in the rotation preventer 2 in such an orientation, that the direction of curvature of the curved deflection section 5 is anteriorly when the rotation preventer 2 is positioned with the support surfaces 15, 16 resting on an abdominal surface 8 and the guidewire 1 generally extending along that surface 8. In practice, the rotation preventer 2 will rest indirectly on the abdominal surface 8 since this surface is in most cases covering by sheet material.

The rounded tip section 4 and the curved deflection section 5 are inserted into a straightener 21, so that a situation as shown in FIGS. 1 and 2 is reached in which the rounded tip section 4 and the curved deflection section 5 are bent into an essentially straight condition. Such straighteners are commercially available and serve for leading a guidewire into a needle without damaging the outer surface of the guidewire.

Figure 7A:
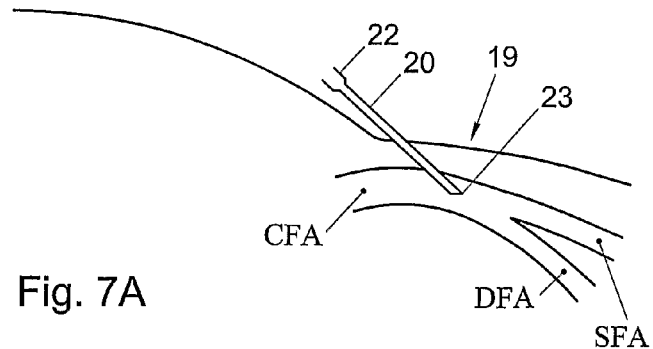
FIG. 7A is a schematic sagittal view of a portion of a patient with a vascular access needle in an oblique, antegrade position after having punctured the CFA.
Figure 7B:
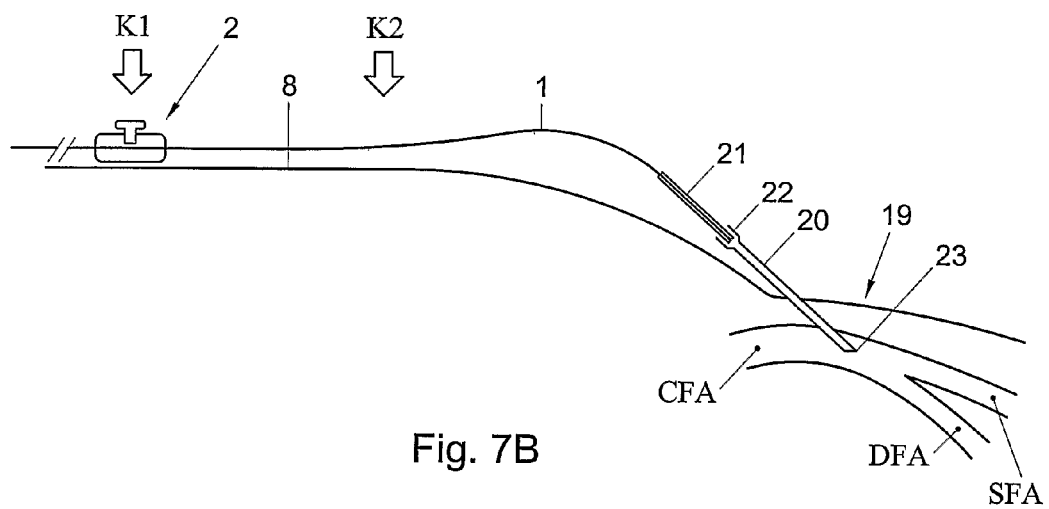
FIG. 7B is a schematic view as seen in FIG. 7A in which a guidewire is guided into the vascular access needle while its orientation is guided by a rotation preventer.
Figure 7C:
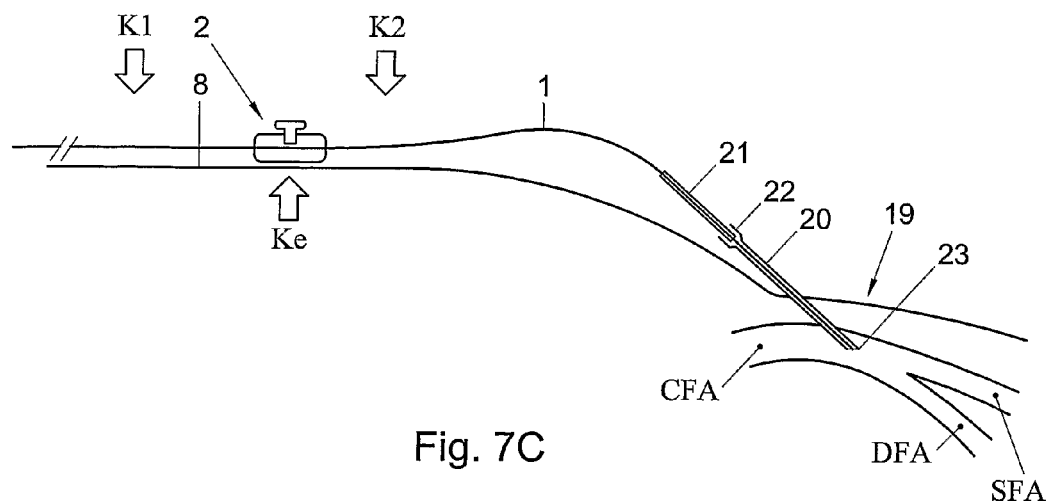
FIG. 7C is a schematic view as seen in FIG. 7B but with the guidewire advanced through the vascular access needle just before the guidewire emerges from the distal end of the needle in the CFA.

Next, a needle 20 is pierced into the CFA obliquely in antegrade direction, so that a situation as shown in FIG. 7A is reached. The needle 20 may for instance be a 18 G vascular access needle. The length of the needle 20 is preferably 5-10 cm and more preferably 7-9 cm.

Then, a distal end portion of the guidewire 1 is inserted into the needle 20. In the present example, this is achieved by placement of the straightener 21 containing a distal end portion of the guidewire 1 into a hub 22 at a proximal end of the needle 20 (see FIG. 7B).

The guidewire 1 is then advanced further through the needle 20 such that the distal end portion emerges from the tip 23 of the needle 20 in the CFA. Since the guidewire 1 has been oriented about its axis such that the direction of curvature of the curved deflection section 5 is anteriorly and the guidewire 1 is held in substantially that orientation by the rotation preventer 2, the orientation in which the guidewire 1 has been inserted into the needle 20 is such that the direction of curvature to which the curved deflection section 5 springs back to substantially its original shape as it emerges from the needle 20 is towards the SFA (see FIG. 7D).

Figure 7D:
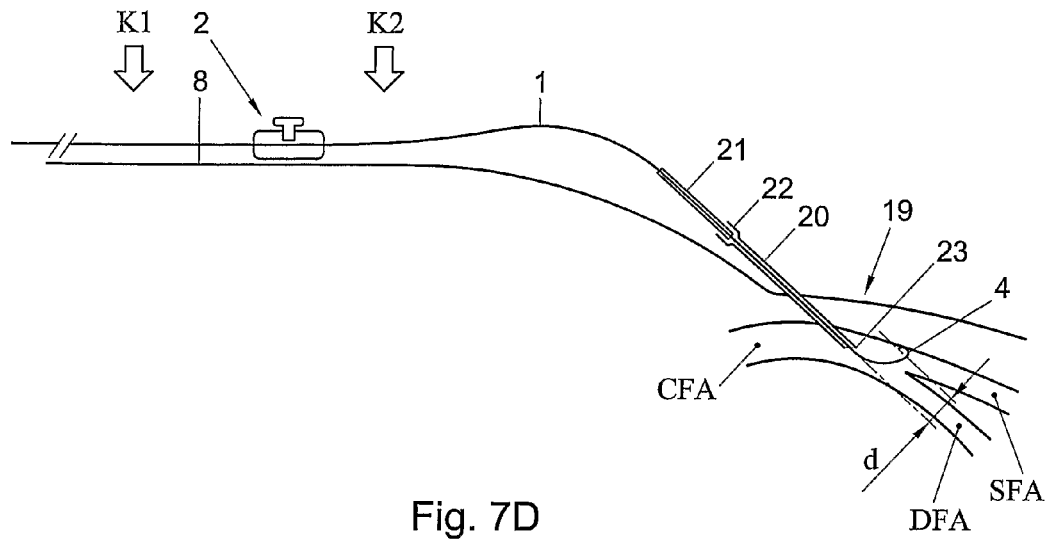
FIG. 7D is a schematic view as seen in FIG. 7C but with the guidewire advanced through the vascular access needle such that a distal end section emerges from the distal end of the needle in the CFA.
Figure 7E:
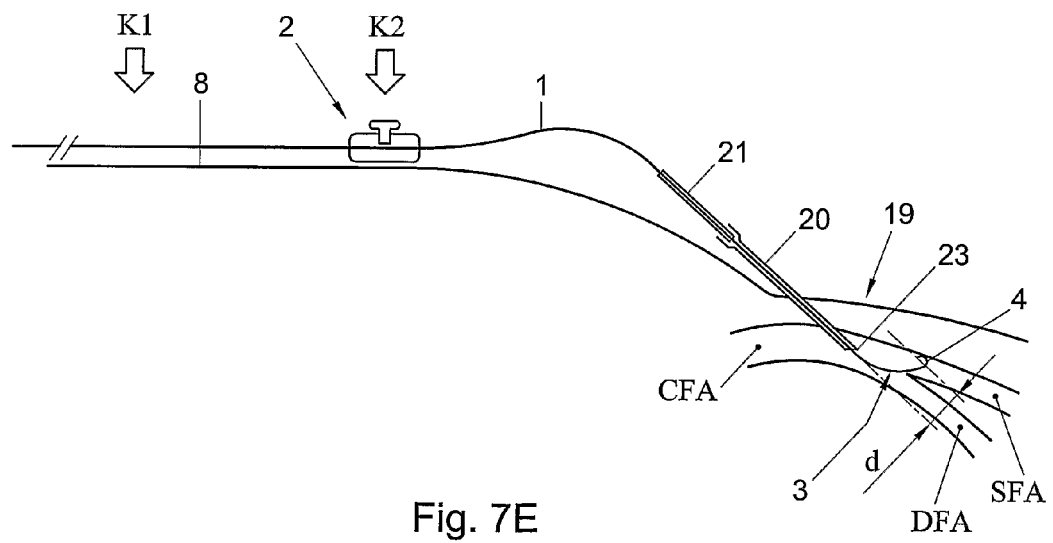
FIG. 7E is a schematic view as seen in FIG. 7D but with the guidewire further advanced through the vascular access needle such that its distal tip has entered the SFA.

The guidewire 1 is then further advanced, so that its tip 4 enters into the SFA (FIG. 7E). The deflection d in FIGS. 7D and 7E is smaller than the deflection d in unloaded condition shown in FIGS. 3 and 5. In FIG. 7D, the curved deflection section is still partially in straightened condition inside the needle 20 and in FIG. 7E, the tip 4 of the guidewire contacts an anterior wall portion of the SFA and is thereby prevented from diverging further from the continuation 6 of the proximally neighboring guidewire section 7.

Until the stage shown in FIG. 7E, no use has been made of fluoroscopy to monitor progress of the guidewire 1. It is however preferred to use fluoroscopic monitoring to check whether the guidewire 1 has actually entered the SFA. Since this can be deferred until the tip 4 of the guidewire 1 has progressed into the SFA over a substantial distance beyond the bifurcation, exposure of the fingers of the operator to X-ray radiation is nevertheless limited. If relevant, further advancement of the guidewire 1 down the SFA may also be monitored using fluoroscopy.

Once the distal end portion of the guidewire 1 has reached the desired position in the SFA, the guidewire 1 can be detached from the rotation preventer 2, by unscrewing the bolt 10 from the rotation preventer 2 and the guidewire 1 can then be pulled out of the passage 9 in the rotation preventer 2.

While keeping the guidewire 1 in position with its tip 4 in the SFA, both straightener and the needle are then removed and subsequently an introducer sheath is moved over the guidewire 1 into the SFA. The patient is then ready for catheterization of the SFA via the sheath.

As is best seen in FIGS. 7D and 7E, the curved deflection section 5 allows the rounded tip 4 of the guidewire 1 to be urged away from the DFA and into the SFA, so that the guidewire 1 reliably enters the SFA without requiring monitored manipulation. More in particular, because the area where the tip 4 of the guidewire 1 is to be deflected in the direction in which the SFA diverges from the DFA is close to the area where the operator grips the guidewire 1, on the one hand, the direction of curvature of the curved deflection section 5 can be controlled easily without relying on X-ray vision to actually see where the guidewire tip 4 is and, on the other hand, by avoiding the need of manipulation, contrast medium injection and fluoroscopic screening near the puncture site, exposure of the operator's fingers to X-ray radiation is substantially reduced.

To effectively deflect the tip of the guidewire 1 towards the SFA, it is preferred that the spacing d between the heart line of the rounded tip 4 and the continuation 6 of the axis of the section 7 proximally neighboring the curved deflection section 5, measured perpendicularly to the continuation 6 of the axis of the section 7 proximally neighboring the curved deflection section 5 and from the continuation 6 of the axis of the section 7 proximally neighboring the curved deflection section 5 to an end of the heart line of the rounded tip 4 most proximal to the curved deflection section 5 is at least 4 mm and more preferably at least 8 mm.

For reliable entry of the tip 4 of the guidewire 1 into the SFA, the curved deflection section 5 preferably extends over at least 45° and more preferably at least 90° and/or the curved deflection section 5 preferably has a radius $R_5$ of at most 30 mm.

For reducing the risk of buckling of the curved deflection section 5, it is advantageous if the curved deflection section 5 extends over at most 165° and more preferably at most 150° and has a radius $R_5$ of at least 5 mm and more preferably at least 8 mm or, yet more preferably, at least 10 mm.

As was observed in *Antegrade Puncture of the Femoral Artery: Morphologic Study* (Spijkerboer A. M., Scholten F.

G., Mali W. P., van Schaik J. P.; Radiology 1990 July; 176(1): 57-60), the distance between the position where the CFA is punctured and the bifurcation into the SFA and the DFA is quite variable and not visible for the operator without body penetrating imaging. Since the bifurcation may be very close to the tip 23 of the needle 20, it is advantageous if the curved deflection section 5 has a distal end located at a distance of less than 5 mm from the rounded tip 4 and more preferably the curved deflection section 5 is located directly adjacent to the rounded tip 4. The closer the curved deflection section 5 is to the rounded tip 4, the earlier the deflection of the rounded tip 4 towards the SFA starts as the guidewire emerges from the tip 23 of the needle 20 and the more effective the deflection is for ensuring that the guidewire enters the SFA, in particular if the bifurcation of the CFA into the DFA and the SFA is very close to the tip of the needle 23.

The total length of the guidewire is preferably 40-60 cm and the length of the curved deflection section 5 is preferably 3 to 5 cm. The flexibility of the curved deflection section 5 in the plane of the curve is preferably equal to the stiffness of the flexible tip of conventional J-guidewires and the curved deflection section 5 is preferably more flexible than the shaft 7 of the guidewire 1.

For ensuring that the direction of curvature is accurately oriented towards the SFA, it is advantageous if the guidewire 1 has a high torque stiffness.

For easy positioning of the guidewire 1 in the passage 9 through the rotation preventer 2 and removal of the guidewire 1 from that passage 9, it is advantageous if the passage 9 is a laterally open groove. this allows the guidewire to be placed in the passage and removed from the passage 9 in lateral direction without having to thread the guidewire 1 axially through the passage 9.

The main body of the rotation preventer 2 may for instance be a substantially rectangular plastic plate (e.g. 10 cm×3 cm×1 cm) and the bolt may for instance be a plastic bolt to avoid damaging the guidewire 1. A clamping jaw member, for instance in the form of a sheath which may be open along axial slit therein, between the bolt and the guidewire (not shown) may be provided to avoid damage due to friction between the bolt and the guidewire as the bolt is tightened and untightened.

A particular advantage of the use of the rotation preventer 2 fixed to the guidewire 1 is, that it can also be used to monitor advancement of the guidewire 1 into the patient.

After the straightener 21 containing a distal end portion of the guidewire and the tip 4 of the guidewire 1 in a known position relative to the ends of the straightener 21 (preferably with the guidewire tip 4 at a distal end of the straightener 21) has been connected to the needle 20 (see FIG. 7B) a marking is positioned at the position K1 of the rotation preventer 2. This marking may for instance be a Kocher's forceps or any other fixable instrument fastened to the sterile drapes on the patients belly. A second marking is then positioned in a position K2 at a distance measured along the guidewire 1 from the position K1, which distance is calculated from the initial distance of the distal guidewire end to the distal end 23 of the needle 20, the ultimate distance over which the guidewire 1 is to project from the needle 20 and, where applicable, guidewire shortening due to the rounded tip 4 springing back to its curved configuration after emergence from the needle 20. Another marking Ke may be positioned at a distance measured along the guidewire 1 from the position K1 that is equal to the initial distance of the distal guidewire end to the distal end 23 of the needle 20. During advancement of the guidewire 1 through the needle 20, the displacement of the rotation preventer 2 from the position K1 to the positions Ke and K2 is monitored and once the rotation preventer 2 has reached the position Ke, the operator knows that the guidewire 1 starts to emerge from the tip 23 of the needle 20 (FIG. 7C), and when the rotation preventer has reached the position K2, the operator knows that the guidewire 1 has been inserted into the SFA over the desired distance (FIG. 7E).

Figure 6:
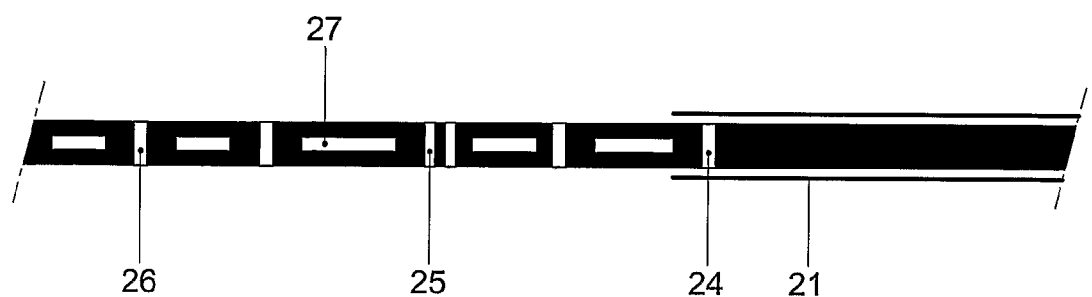
FIG. 6 is an enlarged view of a distal end section of the guidewire projecting into a straightener for guiding a guidewire into a needle.

As illustrated by FIGS. 5 and 6, the guidewire 1 may carry one or more humanly visible insertion depth markings 24-26 each indicating a distance to the distal tip 4 and one or more humanly visible steering aid markings 27 in a position spaced from the curved deflection section 5 and indicating the direction of curvature of the curved deflection section 5. The markings are preferably in a tint contrasting with the general tint of the guidewire and may be of different colors.

The deflection direction markings 27 are provided on the side of the guidewire which is to face anteriorly, so that the deflection direction markings 27 are easily visible when the guidewire 1 is oriented correctly. When a guidewire is equipped with one or more deflection direction markings 27 indicating the direction of curvature of the curved deflection section 5 (in unloaded condition), the guidewire 1 may be introduced without using a rotation preventer 2. Instead, a conventional torque steering device enhancing the operators grip on the guidewire 1 may be used or, depending on the lubricity of the guidewire, the guidewire 1 may be gripped directly.

The combination of using a rotation preventer and at least one longitudinal marking leads to the safest procedure. The rotation preventer keeps the guidewire in the desired orientation while the deflection direction markings offer the operator a visual check whether the guidewire is indeed oriented correctly about its longitudinal axis. The deflection direction marking or markings can also be helpful for quickly fixing the guidewire in the rotation preventer in the correct orientation about its longitudinal axis.

The, preferably transverse, insertion depth markings indicating the distance measured from its tip end 4 may for instance be located as shown in FIG. 5 in which a most distal marking 24 is located at a distance equal to the sum of the length of the straightener 21 and the length of the needle 20 and two more proximal markings 25, 26 at distances from the tip 4 corresponding to projection of the wire tip 4 from the needle 20 over 2 and, respectively, 4 cm. This allows the operator to see when the wire tip 4 enters the artery and subsequently how far the wire tip 4 has entered the vessel lumen without using any fluoroscopy. The tip 4 of the guidewire 1 will enter the CFA (FIG. 7C) when the mark 24 enters the straightener 21. When the mark 26 enters the straightener 21, the wire tip 4 will have entered the SFA in most cases (FIG. 7E).

In individual patients the distances between the level of the center of the femoral head (the 'target' level of entering the CFA in antegrade puncture) and the femoral bifurcation range from 7 to 49 mm with an average of 26 mm (*Antegrade Puncture of the Femoral Artery: Morphologic Study* (Spijkerboer A. M., Scholten F. G., Mali W. P., van Schaik J. P.; Radiology 1990 July; 176(1):57-60)). Consequently, if the CFA is punctured at the mentioned target level, if the needle enters the vessel for 1 cm, and if the guidewire 1 protrudes 4 cm out of the needle 20, the wire tip 4 would have been inside the SFA for all cases reported in this study after insertion of the guidewire until the most proximal insertion depth mark 26 is at the entrance of the straightener 21.

It is observed, that within the framework of the present invention many other embodiments are conceivable. For instance, the rotation preventer may be adapted to be guided in a guide rail. Also, the tip may be provided in another form than a J-shaped end of the guide wire, such as in the form of a floppy end which is substantially more flexible than the curved deflection section and may be in an essentially straight configuration when in unloaded condition. Also, the curved deflection section may consist of two or more curved sections spaced from each other along the length of the guidewire or the radius of curvature may increase gradually along the guidewire from a smallest radius of curvature at the rounded tip to a larger radius of curvature of the curved deflection section. Furthermore, the transverse markings may be positioned to indicate the position of the tip of the guidewire relative to the distal tip of the needle when aligned with another part than the proximal end of the straightener, such as markings on the straightener or the needle hub if the straightener or the needle hub is transparent or equipped with a window through which the marking can be seen.

The invention claimed is:

1. A method of antegrade insertion of a guidewire via a common femoral artery into a superficial femoral artery of a human patient, the superficial femoral artery branching off from the common femoral artery anteriorly of a deep femoral artery, comprising:
   piercing a needle into the common femoral artery with a tip of the needle pointing obliquely in antegrade direction relative to the common femoral artery, the needle bounding a lumen oriented in an axial direction of the needle;
   providing a guidewire having a tip structure at its distal end and a curved deflection section located proximal of the tip structure at a distance of less than 5 mm from a proximal end of the tip structure,
      wherein the tip structure is selected from the group consisting of:
         a rounded tip having, when in an unloaded condition outside the needle, a radius larger than the guidewire circumference radius, and
         a floppy tip section having more flexibility than a proximally adjacent section of the guidewire,
      wherein the curved deflection section has, when in the unloaded condition, a radius of curvature of at least 5 mm and at most 30 mm and extending over an angle of curvature of at least 90° such that the tip is spaced from a continuation of an axis of a section of the guidewire proximally neighboring the curved deflection section, and
      wherein the curved deflection section has a flexibility causing the curved deflection section to spring back to substantially its original curved shape when released from the distal end of the needle or another bounding lumen after elastic deformation to a straightened condition,
   inserting a distal end portion of the guidewire into the lumen of the needle and urging the guidewire through the needle such that the distal end portion emerges in an axial direction of the needle from a distal end of the lumen of the needle into the common femoral artery, the guidewire being in a predetermined rotational orientation about a center line of the guidewire such that the curved deflection section springs back from the straightened condition inside the needle, as the guidewire distal end emerges from the needle, in an anterior direction towards its original curved shape, and
   advancing the guidewire wherein the tip of the guidewire deflects towards the anterior wall of the common femoral artery, contacts the anterior wall of the common femoral artery, contacts the anterior wall of the superficial femoral artery and enters the superficial femoral artery.

2. The method according to claim 1, wherein progress of the guidewire tip structure is monitored fluoroscopically only after the guidewire tip structure has passed the bifurcation of the common femoral artery into the superficial femoral artery and the deep femoral artery.

3. The method according to claim 1, further comprising:
   prior to insertion of the guidewire into the lumen of the needle oriented obliquely in antegrade direction, fixing the guidewire to a rotation preventer having support areas and bounding a passage accommodating a section of the guidewire preventing rotation of the guidewire from rotation about its axis relative to the rotation preventer,
   positioning the rotation preventer with the support areas supported by an abdominal surface of the patient, the direction of curvature of the curved deflection section being oriented anteriorly.

4. The method of claim 1 wherein the rounded tip is a guidewire section having a radius of 1-4 mm when the guidewire is in the unloaded condition.

5. The method of claim 1 wherein a spacing between a proximal end of the tip structure and a continuation of an axis of a guidewire section proximally neighboring the curved deflection section is at least 4-8 mm when the guidewire is in the unloaded condition, the guidewire tip contacting an anterior wall of the common femoral artery while the curved deflection section is still partially straightened in the lumen of the needle.

6. The method of claim 1 wherein the curved deflection section extends over at most 165° when the guidewire is in the unloaded condition.

7. The method of claim 1, wherein the curved deflection section is located directly adjacent to a proximal end of the tip structure.

8. The method of claim 1, wherein during the inserting step the distal end portion of the guidewire is inserted into the lumen of the needle in a predetermined orientation about a centre line of the guidewire such that the distal end portion emerges in the axial direction of the needle from the distal end of the lumen of the needle into the common femoral artery.

* * * * *